(12) United States Patent
Paolino et al.

(10) Patent No.: US 10,098,923 B2
(45) Date of Patent: Oct. 16, 2018

(54) *DAPHNE LAUREOLA* EXTRACTS IN THE TREATMENT OF DERMOPATHIES (71) Applicants: Donatella Paolino, Pedara (IT); Gioacchino Folino Gallo, Martirano Lombardo (IT); Massimo Fresta, Montepaone (IT); Leone Spataro, Falema (IT)

(72) Inventors: Donatella Paolino, Pedara (IT); Gioacchino Folino Gallo, Martirano Lombardo (IT); Massimo Fresta, Montepaone (IT); Leone Spataro, Falema (IT); Alessandro Venditti, Fontana Liri (IT)

(73) Assignees: Donatella Paolino, Pedara (IT); Gioacchino Folino Gallo, Martirano Lombardo (IT); Massimo Fresta, Falema (IT); Leone Spataro, Falema (IT)

( * ) Notice: Subject to any disclaimer, the term of this patent is extended or adjusted under 35 U.S.C. 154(b) by 55 days.

(21) Appl. No.: 15/100,104

(22) PCT Filed: Nov. 26, 2014

(86) PCT No.: PCT/IT2014/000312
§ 371 (c)(1),
(2) Date: May 27, 2016

(87) PCT Pub. No.: WO2015/079469
PCT Pub. Date: Jun. 4, 2015

(65) Prior Publication Data
US 2017/0000838 A1   Jan. 5, 2017

(30) Foreign Application Priority Data
Nov. 27, 2013 (IT) .............. RM2013A0657

(51) Int. Cl.
| | | |
|---|---|---|
| *A61K 36/00* | (2006.01) |
| *A61K 36/83* | (2006.01) |
| *A61K 9/00* | (2006.01) |
| *A61Q 5/00* | (2006.01) |
| *A61Q 19/00* | (2006.01) |
| *A61K 8/97* | (2017.01) |
| *A61K 9/06* | (2006.01) |
| *A61K 9/107* | (2006.01) |
| *A61K 8/02* | (2006.01) |

(52) U.S. Cl.
CPC ............ *A61K 36/83* (2013.01); *A61K 8/0216* (2013.01); *A61K 8/97* (2013.01); *A61K 9/0014* (2013.01); *A61K 9/06* (2013.01); *A61K 9/107* (2013.01); *A61Q 5/006* (2013.01); *A61Q 19/008* (2013.01); *A61K 2236/00* (2013.01); *A61K 2236/33* (2013.01)

(58) Field of Classification Search
CPC ...................................... A61K 36/00
See application file for complete search history.

(56) References Cited

U.S. PATENT DOCUMENTS

2006/0165819 A1 * 7/2006 Meisner ............ A61K 31/4745
424/725.1

FOREIGN PATENT DOCUMENTS

KR   839030 B1 * 6/2008

OTHER PUBLICATIONS

Touati et al, Flavanoids in Daphne laureola L. Plantes Medicinales et Phytotherapie, (1993) vol. 26, No. 1, pp. 43-48.*
Jaric et al, An ethnobotanical study on the usage of wild medicinal herbs from Kopaonik Mountain (Central Serbia). Journal of ethnopharmacology, (Apr. 20, 2007) vol. 111, No. 1, (Year: 2007).*

* cited by examiner

Primary Examiner — Qiuwen Mi
(74) Attorney, Agent, or Firm — Greer, Burns & Crain, Ltd.; Gregory P. Einhorn (57) ABSTRACT The invention relates to an extract obtained from *Daphne laureola* L to be used the pharmaceutical cosmetic and cosmeceutical field for the topical treatment of dermopathies in general and of psoriasis in particular, by means of the topical application of effective amounts of said extracts. The invention also relates to the pharmaceutical, cosmetic and cosmeceutical compositions comprising the *Daphne laureola* extracts. The invention also relates to the topical treatment of dermopathies in general and of psoriasis in particular.

16 Claims, 5 Drawing Sheets

DAPHNE LAUREOLA EXTRACTS IN THE TREATMENT OF DERMOPATHIES

This application is a national phase application claiming benefit of priority under 35 U.S.C. § 371 to International (PCT) Patent Application serial number PCT/IT014/000312, filed Nov. 26, 2014, which claims benefit of priority to Italian patent application serial number RM2013A000657, filed Nov. 27, 2013. The aforementioned applications are expressly incorporated herein by reference in their entirety and for all purposes.

FIELD OF THE INVENTION

The present invention relates to the treatment of dermopathies such as for example psoriasis and dandruff by means of treatment with a vegetal extract of *Daphne laureola*. More in general the invention relates to the topical use of the phytocomplex extracted from *Daphne laureola* in therapy and for personal and animal hygiene. Within the scope of the present invention with phytocomplex is meant the whole of the substances obtained by extraction from plants that can be used in the pharmaceutical, cosmeceutical and cosmetic field. Within the scope of the present invention the term extract and the term phytocomplex are considered synonyms.

BACKGROUND ART

Dermopathies are an important sanitary issue whose incidence is steadily increasing. Dermopathies comprise cutaneous affections characterized by cell hyperproliferation, such as e.g., psoriasis, dandruff, skin tumors and actinic keratosis.

The most frequent among the dermopathies are psoriasis and dermatitis, such as for example:
Atopic dermatitis: usually of psychosomatic origin.
Contact dermatitis: It is a reaction of the body to specific allergens with which it gets into contact. It manifests itself with redness, scabs and skin desquamation.
Seborrhoic dermatitis: this type involves mainly body areas more prone to sebum secretion, such as for example the scalp.
Chronic dermatitis: it is an inflammatory reaction with activation of the immune system which involves the skin and shows itself initially as an irritation spread to different body parts and has a chronic progress, of the relapsing type.
Non-specific dermatitis: it can be occasional and shows with redness and/or desquamation, possibly with itching, that can not be related to precise pathological causes.

Psoriasis is a widespread pathology and is one of most common types of chronic dermatitis that involves skin and in particular the stratum corneum. From an etiopathological point of view it is an inflammatory reaction with activation of the immune system which affects the skin and initially shows itself as an irritation spread to different parts of the body.

Psoriasis is not an infective pathology but generally shows with a chronic progress of the relapsing type. It is characterized by the occurrence of red and desquamating spots that are localized to some body parts such as elbows, hand palms, knees, feet soles and scalp.

Psoriasis prevalence in the general population is estimated to be between 1 and 3%, in general one third of the patients shows with the first appearance of psoriasis already during infancy or adolescence.

The etiology of psoriasis is still unknown and the available data seem to point to a multifactorial origin; genetical and environmental factors are, as a matter of fact, involved in the onset and progress of this pathology.

Psoriasis can be considered an hereditary disease with a familial tract.

Psoriasis occurs with a varied symptomatology. This pathology can, as a matter of fact, occur as:
Plaque psoriasis: the most common type from a clinical point of view; the typical lesion is a well defined erythematous plaque covered with silvery desquamating scales, similar to mica. The single plaques can have different diameters and can merge to cover whole body areas.
Guttate psoriasis: it occurs in young subjects after a streptococcal tonsillar infection. 1 mm to 1 cm papulae appear on the skin mainly on the body trunk having the appearance of raindrops.
Pustular psoriasis: this type can occur with a localized or generalized character; in particular, the former occurs mainly on the hand palms and on feet soles. In this case small subcorneal vesicles appear that get to the surface and desquamate.
Erythrodermal psoriasis: this is a serious type of psoriasis where all the skin surface becomes erythematous and desquamated. This type can be caused by drugs, stress, concurrent diseases.
Seborrhoic psoriasis: a very common type also called sebopsoriasis or seboriasis. It is characterized by lesions that are very similar to seborrhoic dermatitis, but can involve areas that normally are not involved.
Psoriasis amiantacea: it is a type that only involves the scalp. Usually it is a juvenile affection.

Psoriatic lesions usually occur hystologically as hyperproliferating areas, with a 10-fold increased epidermal turnover with respect to normal skin, with and incomplete maturation of keratinocytes and nuclei retained in the stratum corneum (parakeratosis), with neovascularization processes, increased blood flow, protein exudates and immature lymph vessels. The appearance of psoriatic plaques on skin surface is also linked to polymorph neutrophils infiltration in the epidermis. In addition, the healthy skin in psoriatic patients shows with structural modifications and in these subjects the progress of the pathology has a favorable progression after the occurrence of a traumatic event (Koebner phenomenon). Also, psoriatic subjects have more intense turnover cycles with respect to those not affected by this pathology and show an increased cell DNA synthesis and higher glycogen levels in the lesions with respect to the skin from non-psoriatic subjects.

This effect seems to be related with the functional modification of the cell-mediated immune system (T lymphocytes) and of the epidermal response to cytokines that carry out a fundamental role in the genesis and progress of this disease.

Cytokines are protein molecules produces by different cell types and are secreted in the surrounding medium, usually in response to a specific stimulus; they are able to modulate the behavior of different cells by stimulating their growth, differentiation and death. Their action is usually local, but sometimes they have a beneficial effect on the whole body. Interleukins have an etiopathogenic role in different diseases that have been discovered in the last few years; as a matter of fact, T cells that produce type 1, 6 and 8 interleukins have an important role in the pathogenesis of psoriasis. In particular interleukin 6 (IL-6) is a pleiotropic cytokine produced by many cell types among which monocytes/macrophages, fibroblasts, endothelial cell, keratinocytes, T cells, B cells, neutrophils.

Current therapies for dermopathies in general and for psoriasis in particular provide biomedical approaches that include as first-line drugs in the limited-extension types topical emollient preparations such as vaseline, cortisone formulations and/or reducing agents (tar or ditranol), keratolytic agents (salicilic acid and/or urea) and vitamin D analogs. In the case of generalized types of psoriasis, sometimes systemic therapies are used such as phototherapy with UVB or UVA and psoralens (photochemotherapy or PUVA therapy), retinoid use (acitretin and etretinate) or cyclosporin A.

Biological drugs have been recently introduced such as monoclonal antibodies, cytokines (interferons and interleukins), fusion proteins and tissue growth factors.

*Daphne laureola* L., (Italian: *dafne laurella*), is a species of *Daphne*, in the Thymelaeaceae family. It is an evergreen plant with green-yellowish flowers that mature into black berries in the late summer. *D. laureola* L. (DL) can be from 50 to 150 cm in height. The bark is thin and grey-yellowish when mature, while the young branches are green. The alternate inserted leaves usually give thick spirals toward the top of the buds, but can also cover whole branches. The leaves are lanceolated or oboval-lanceolated, 2-13 cm in length and 1-3 cm in width. They are hairless, dark green, shiny on the upper face and brighter on the lower face. It grows both in the sun and in the shadow and it gets easily adapted to the temperate underwood. The reproduction can be both by seed and by radical sprouts.

It is known in the prior art (CN 101181427) the antipsoriatic action of extracts obtained from a combination or different plants. Among the different components of this mixture *Daphne genkwa* (DG) can be found, a plant from Asia and belonging to the same family as DL, but, unlike DL that is an evergreen, this plant is deciduous. It is also distinguished from DL for its flowers of an unusual lilac-blue with amethyst hues.

It is also known from a very old patent application (GB 479688, dated 1936) the use of DL for the treatment of eczema in animals. Anyway, it is described the use of leaves, simply dried or withered, to be mixed with animal fodder, pointing thus to an oral use. This approach is not applicable to the use in humans since DL and other species of *Daphne* resulted as toxic if ingested, so that their oral use in humans is not advisable ("*Natural remedies and Nutriceuticals Used in Ethnoveterinary Practices in Inland Southern Italy*"—Pieroni et al.).

The ingestion of *Daphne* has very serious consequences and can be lethal as reported by et al. in "*Isolation and structure of daphnetoxin, the poisonous principle of Daphne species*".

It was thus felt the need for a product that could be used topically and that could have an increased effectiveness with respect to the prior art to dermopathies in general and in particular to skin tumors and psoriasis and that could be useful not only in the pharmaceutical field, but also for personal hygiene in all the skin diseases related to dermopathies.

SUMMARY OF THE INVENTION

The present invention proposes the topical application of a DL extract for the treatment of dermopathies in general and of psoriasis in particular. The DL extract was compared in vitro to that of *Daphne genkwa* (DG). These two plants have a different origin and geographical distribution, they are distinguished by different features, DL is an evergreen, DG is a deciduous plant and it is also distinguished by its flowers of an unusual lilac-blue with amethyst hues.

Comparing these two plants DL appeared to be unexpectedly more effective.

The present invention provides a valid natural alternative to the current therapies that unfortunately nowadays are not satisfactory, in particular for psoriasis.

It is therefore an object of the present invention an extract obtained from *Daphne laureola* to be used in the pharmaceutical, cosmetic and cosmeceutical fields.

The extracts of the invention can be used alone or in combination with different active principles known to the expert in the field. Formulated for the topical use they are able to effectively and rapidly improve skin diseases with no need for oral administration and with no side effects.

A further object of the invention are the pharmaceutical, cosmetic and cosmeceutical compositions comprising the phytocomplex obtained by extraction from *Daphne laureola*.

A still further object of the invention is a method for the pharmaceutical, cosmetic and cosmeceutical treatment of dermopathies in general and of psoriasis in particular comprising the topical application of effective amounts of the phytocomplex obtained by extraction from *Daphne laureola*.

A still further object of the present invention is the use of the phytocomplex obtained by extraction from *Daphne laureola* in the pharmaceutical cosmetic and cosmeceutical field for the treatment of dermopathies in general and of psoriasis in particular, by means of the topical application of effective amounts of said phytocomplex. The use of the phytocomplex is also convenient for the treatment of skin diseases characterized by cell hyperproliferation, such as, for example, psoriasis, dandruff, skin tumors and actinic keratosis.

Further objects of the present invention are pharmaceutical, cosmetic and cosmeceutical kits, comprising at least one product, preferably at least two products containing the phytocomplex or the extract of the invention containing it, chosen from: shampoo, cleansing milk, aqueous tonic, aqueous solution, alcoholic solution, hydroalcoholic solution, mask, emulsion, water-based gel, lipogel, face and body oil, medicated patches.

Further objects will be evident from the following Detailed Description of the Invention.

DETAILED DESCRIPTION OF THE INVENTION

The extracts containing the DL phytocomplex according the invention are obtained from plants, preferably not blooming. The extracts are preferably obtained from the leaves, anyway all the plant's part can be used: flowers, fruits, leaves, stalk and roots, both fresh and dried. After harvest the samples can be used fresh, usually after rinsing or can be dried in a stove (for example a ventilated stove at 22° C. until completely dehydrated).

The extracts of the invention can be prepared according to the methods traditionally used in the field of natural products extraction known to the expert in the field, such as, e.g., described in "*Botanicals, a Phytocosmetic Desk Reference*" Frank S. D'Amelio, CRC Press, pg. 39-48.

The solvents that should preferably be used to carry out the extraction are the solvents usually employed in the herbal field, such as, e.g., polar solvents, for example chosen in the group comprising: water, ethanol, glycerol, propanol, butanol, acetone, glycols such as ethylene-, propylene- and butylenes-glycol, ethylacetate, hexane, methylene chloride, methanol, different ethers and correspondent mixtures. Particularly preferred are water or a solvent mixture of ethanol and water in any proportion.

Particularly suitable are the extraction techniques by infusion, decoction and maceration as described herein below.

Infusion is the most simple and fast extraction technique. It provides drug steeping (leaves and/or other parts of the plant, fresh or dried) in previously boiled water for a period of time ranging from 10 min to about 30 min in a preferably covered or sealed container. After the prefixed time, depending from the consistency of the vegetal tissues used, shorter for flowers, tender leaves and finely chopped plant tops as for herbal teas, a little longer for harder and tougher parts, the preparation is filtered lightly pressing the residue: the solution thus obtained is the infusion containing the phytocomplex.

A decoction is prepared steeping the drug in cold water and bringing it to a boil, in a preferably covered or sealed container, for a time ranging from 10 to 60 min. After filtering and lightly pressing the residue and the solution thus obtained is the decoction containing the phytocomplex.

An extract by maceration of the fresh plant is obtained steeping the drug in an alcoholic or hydroalcoholic solution, usually for 24 h or longer.

The infusion, decoction and the extract by maceration can then be concentrated by evaporation or lyophilization of the solution, to obtain very or less concentrated or dry extracts, according to the amount of the residual solvent.

It is also possible to use other extraction methods commonly used in the industrial field, such as percolation or extraction under continuous agitation assisted by ultrasound and/or microwave that bring to extracts containing at least 0.5% in weight of total dry residue, extraction by means of supercritical fluids. It is not necessary to use any pressure.

The extract can be used as it is or can be subjected to different degrees of concentration to dryness to obtain a fluid, semifluid or dry extract. Dryness can be attained by methods traditionally used in this field, such as, e.g., reduced pressure evaporation, spray-drying and lyophilization. The extracts can have such a concentration that to 1 gram of extract correspond 1 to 1.5 gram of fresh drug.

Dry extracts represent the most concentrated form of the phytocomplex and usually are in form of a dehydrated powder, so that they are more stable and can be reconstituted by adding water or another solvent suitable for the use according to the invention, such as, for example, ethanol.

The extract made as described above, containing the DL phytocomplex, can be used as an active principle, alone or in combination with other active principles to prepare compositions to be used both in the medical and in non-medical fields.

The formulations can be chosen among, but are not limited to: shampoo, cleansing milk, aqueous tonic, aqueous solution, alcoholic solution, hydroalcoholic solution, mask, emulsion, water-based gel, lipogel, face and body oil, medicated patches containing an amount of phytocomplex from 1% to 90%.

Other active principles that can be used are chosen among those commonly used in the pharmaceutical, cosmetic and cosmeceutical field, for example: antioxidants, essential oils, vitamins, UV filters, collagen, elastin.

The compositions can be used for topical administration in the form of liquid formulations, such as, e.g., gels, lotions, milks, emulsions, foams and similar; solid or semisolid formulations, such as creams, ointments, sticks and similar. Said formulations can be prepared according to conventional methods, e.g., as described in "*Remington's Pharmaceutical Handbook*", Mack Publishing Co., NY, USA, e "*Botanicals, a Phytocosmetic Desk Reference*" Frank S. D'Amelio, CRC Press, pg. 299-305, together with other pharmaceutically, cosmeceutically and cosmetically accepted components, such as emollients, moisturizers, thickeners, emulsifiers, colorings, detergents, disinfectants, antioxidants, buffers, mattifying agents, exfoliating agents, aromas and similar, essential oils, vitamins, UV filters, collagen, elastin and mixtures thereof.

Examples of compositions are given in the Examples and are herein below briefly reported:
Cleansing milk containing from 0.1 to 5% of dry extract;
Emulsion containing from 0.5 to 10% of dry extract;
Water-based gel containing from 5 to 20% of dry extract;
Aqueous lotion containing from 0.5 to 20% of dry extract;
Medicated patch containing from 5 to 2% of dry extract;
Shampoo containing from 0.5 to 10% of dry extract.

The extracts of the invention are advantageously used as non-purified isolates, keeping substantially intact their biological complexity.

The extracts and corresponding pharmaceutical cosmetic and cosmeceutical compositions if the invention were shown to be particularly effective in the prevention and in the treatment of dermopathies in general, among which the most frequent types are dermatitis, such as atopic dermatitis, contact dermatitis, seborrhoic dermatitis, chronic dermatitis and non-specific dermatitis; dandruff; actinic keratosis; skin tumors such as melanomas, basocellular carcinoma, spinocellular or squamous cell carcinoma; and psoriasis in its different forms, such as plaque psoriasis, guttate psoriasis, pustular psoriasis, erythrodermal psoriasis, seborrhoic psoriasis and amiantaceous psoriasis.

All the body parts are involved in these pathologies, in particular the red and desquamating spots are localized to parts such as elbows, hand palms, knees, feet soles, and scalp.

The affected subjects can also be infants or adolescents and this type of pathologies also presents in animals.

DL extracts according to the invention can be applied alone or in combination with topical emollient preparations such as vaseline, cortisone formulations and/or reducing agents (tar and ditranol), keratolytic agents (salicilic acid and/or urea) and vitamin D analogs; systemic therapies such as UVB phototherapy or UVA phototherapy with psoralens (photochemotherapy or PUVA therapy), retinoid use (acitretin and etretinate) or cyclosporin A; monoclonal antibodies, cytokines (interferons and interleukins), fusion proteins and tissue growth factors.

The convenience of the present invention is due not only to the particular effectiveness of the *Daphne laureola* phytocomplex, but also to the fact that the therapeutic action is exerted at the topical level, with no oral administration. In addition, an important advantage as shown by our experimental observation, the pathology does not seem to show again for at least six months after the treatment's suspension. A further advantage is found in the higher pharmacological effectiveness of *Daphne laureola* with respect to the other plants of the genus *Daphne*.

The present invention will be herein described with reference to the following examples, that are not to be considered as limiting the scope of the invention.

Experimental Part

Decoction Preparation

The DL and decoctions were prepared steeping the fresh plant's leaves in 5% w/v in water (50 g of fresh leaves in 1000 ml of water), bringing to a boil for about two hours until the volume was reduced to a half. The decoction was left to cool and then filtered.

Extracts Preparation by Maceration

The extract was obtained from the fresh plant by maceration at room temperature for 24-48 h in 96% ethanol (200 gr of fresh plant per 1 lt of solvent) (wide range solubilizing solvent for polar and non-polar compounds), extracting three times the vegetal material (complete extraction) and pooling the extracts in one total extract after eliminating the extraction solvent. 96% ethanol was chosen as solvent to extract all the secondary component classes present in the vegetal matrix.

In Vitro Evaluation of Antipsoriatic Activity

The in vitro evaluation of the antipsoriatic activity was carried out in human keratinocytes (NCTC2544), (Emilia and Lombardia Experimental Zooprophylactic Institute). NCTC2544 were seeded in Petri dishes (diameter 100 mm) and incubated using D-MEM culture medium (GIBCO, Invitrogen Corporation, U.K.), with penicillin (50 U/ml), streptomycin (50 µg/ml), non-essential aminoacids, amphotericin B (50 µg/ml) and bovine fetal serum (FBS) at 10% v/v. The incubation was carried out in a cell incubator at 37° C. with 5% $CO_2$. The cells were cultured for three days to allow the cell model to reach 80% confluency. After three days in incubation the cells were detached from the Petri dishes using 1 ml of trypsin/EDTA and transferred in 15 ml centrifuge tubes. 2 ml of culture medium were used to neutralize the human keratinocytes. The Petri dishes were washed using 2 ml of phosphate buffer (PBS), without calcium and magnesium, that were then transferred to the centrifuge tubes. The cell suspension thus obtained was centrifuged at 1000 rpm for 10 minutes at room temperature using a Megafuge 1.0 centrifuge (Heraeus Sepatech, Osterode/Harz, Germany). The cell pellet obtained was resuspended in 6 ml of culture medium to obtain a cell suspension at a final concentration of $1 \times 10^6$ cells/ml. 200 µl of a cell suspension of 2500 cells/well were then seeded in 96-well plates and incubated for 24 h at 37° C. at 5% $CO_2$ to allow for adhesion.

The experimental model to evaluate antipsoriatic activity was developed stimulating fibroblasts with interleukin-6 (IL-6). IL-6 was produced in bacterial cell cultures and the system was purified using a method already described in literature (Arcone et al., 1991). NCTC2544 cells were treated for 48 h with a 0.7 µg/ml concentration of IL-6 at 37° C. with 5% $CO_2$. After a 48 h incubation, NCTC2544 cells wee treated with increasing concentrations of decoction previously lyophilized (0.01, 0.1, 1, 10% w/v) for 48 and 96 h. As an internal control, a culture of untreated human keratinocytes was used at the same concentration as the one used to develop the experimental model. In the case of DL it was also evaluated the antipsoriatic activity of the alcoholic extract obtained by maceration. The in vitro antipsoriatic activity of the formulations was measured by means of the MTT assay. In particular, NCTC2544 cells contained in the different wells were treated with 10 µl of a solution of tetrazolium salts solubilized in PBS and incubated for 4 h at 37° C. at 5% $CO_2$. After 4 h of incubation, the formazan crystals precipitated to the bottom of the wells were solubilized with 200 µl of an ethanol/dimethyl sulphoxide solution and the decrease in proliferation was measured as cell viability by spectrophotometrically measuring the cell concentration at excitation $\lambda$ 540 nm and emission $\lambda$ 690 nm. The proliferation decrease was correlated to the amount of formazan crystals obtained that is directly proportional to the cell absorbance.

The decrease in the percent proliferation was determined using the following equation:

$$\% \text{ Decrease} = (\text{Abs}T/\text{Abs}U) \times 100;$$

where AbsT is the treated cells absorbance and AbsU is the untreated cells absorbance. The percent increase in the cell proliferation obtained is the average of three different assessments±standard deviation.

The in vitro evaluation assays were carried out measuring the decrease in the cell number after the treatments with the decoction or the extract obtained by maceration at different percent concentrations.

Figure 4A:
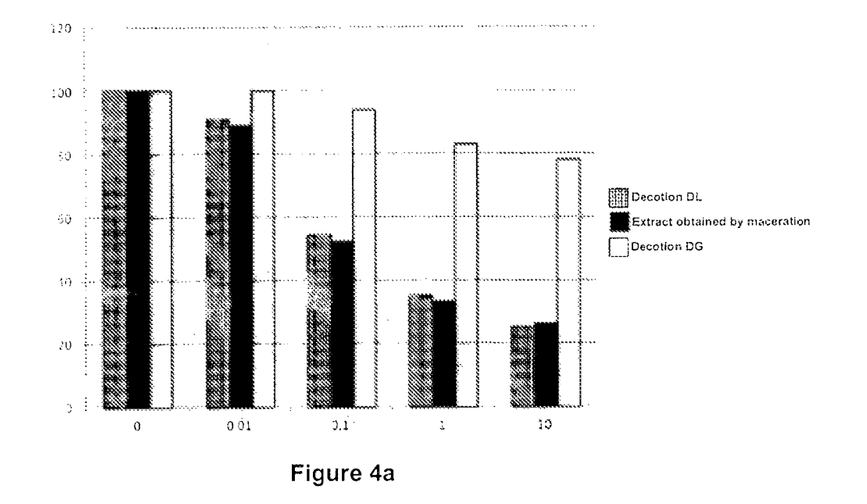
FIG. 4: Evaluation of the in vitro anti-psoriatic activity after 48 hours of treatment with DL and DG decoctions and extracts obtained by maceration of DL in a psoriasis model
Figure 4B:
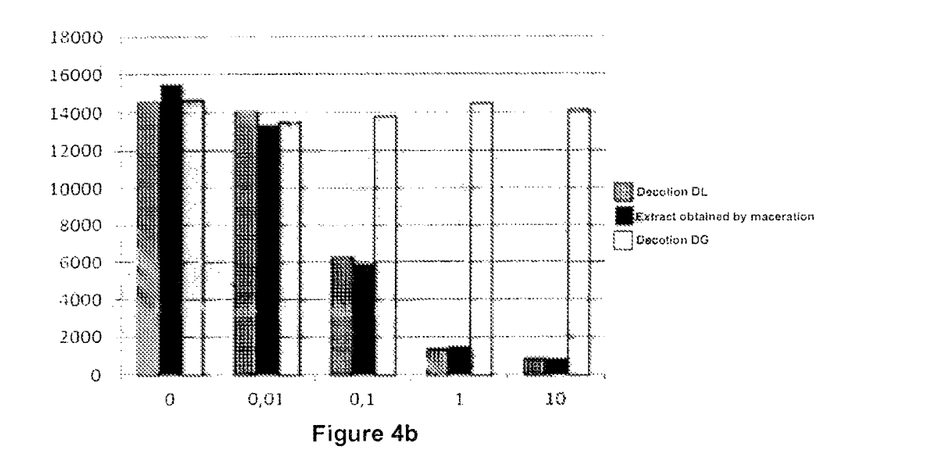

The experimental results obtained showed that the effect on growth inhibition produced by the DL decoction and maceration extract solutions is both time and dose-dependent. The treatment of NCTC2544 cells stimulated with IL-6 at 0.7 µg/ml for 48 h, induces a decrease in growth of 50% with the decoction and of 52% with the maceration extract, after 48 h of treatment at a concentration of 0.1% v/v. The results obtained in terms of reduction of percent growth are more evident increasing the decoction or maceration extract percentage used, 35 and 33 for the 1% concentration, and 25 and 26 for the 10% concentration v/v (FIG. 4a). This dose-dependent effect is likely to be produced by an increased amount of the phytocomplex able to interact with the psoriasis experimental model that takes place when the decoction or maceration extract percentage, used for the treatment increases.

A result, similar to the one obtained for the percent inhibition of growth, was obtained expressing the antipsoriatic activity of the decoction as a function of cell number. In this case the number of NCTC2544 keratinocytes decreased from 14499 cells (control sample) to 6233, 1344 and 787 cells/0.1 ml (samples treated, respectively, with decoction solutions at 0, 1, 1 and 10% v/v).

The DL decoction was compared to a DG decoction prepared following the same procedure and used in the same conditions. At every concentrations and at all the exposure times, the DL extract showed a significantly higher effect with respect to the DG decoction. As a matter of fact, DL at the concentration of 0.1% of decoction solution showed a more than two-fold higher keratinocytes growth percent inhibition with respect to DG. For this reason the following in vivo experimentation was carried out only with the DL decoction.

In Vitro Evaluation of DL Decoction Toxicity

The DL decoction toxicity was assayed after 24, 48 and 72 h of incubation as a function of the v/v product percentage used. Increasing concentrations of decoction previously lyophilized (0.01, 0.1, 1, 10% w/v) were assayed using the MTT assay described above. The compound toxicity was evaluated as a function of the percent viability. The values obtained are the average of six different experiments±standard deviation.

Figure 1:
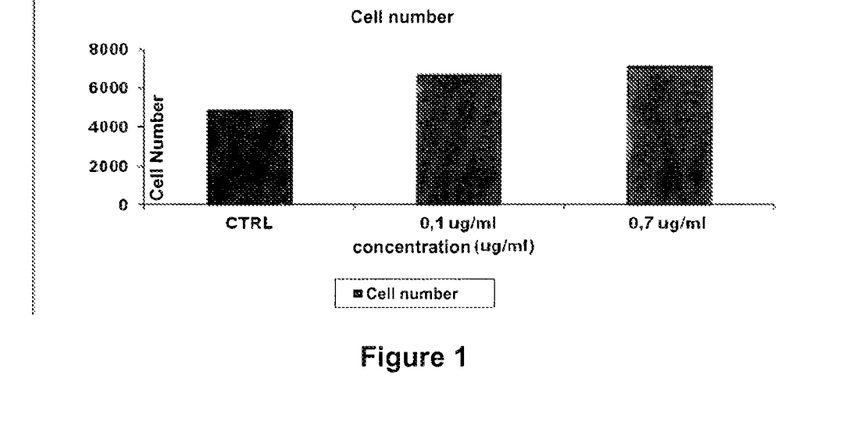
FIG. 1: Stimulation of human keratinocytes (NCTC2544 cells) with IL-6 (0.1 and 0.7 µg/ml): A) Percent proliferation; B) Cell number. Each experiment is the average of three different assessments standard deviation.
Figure 2:
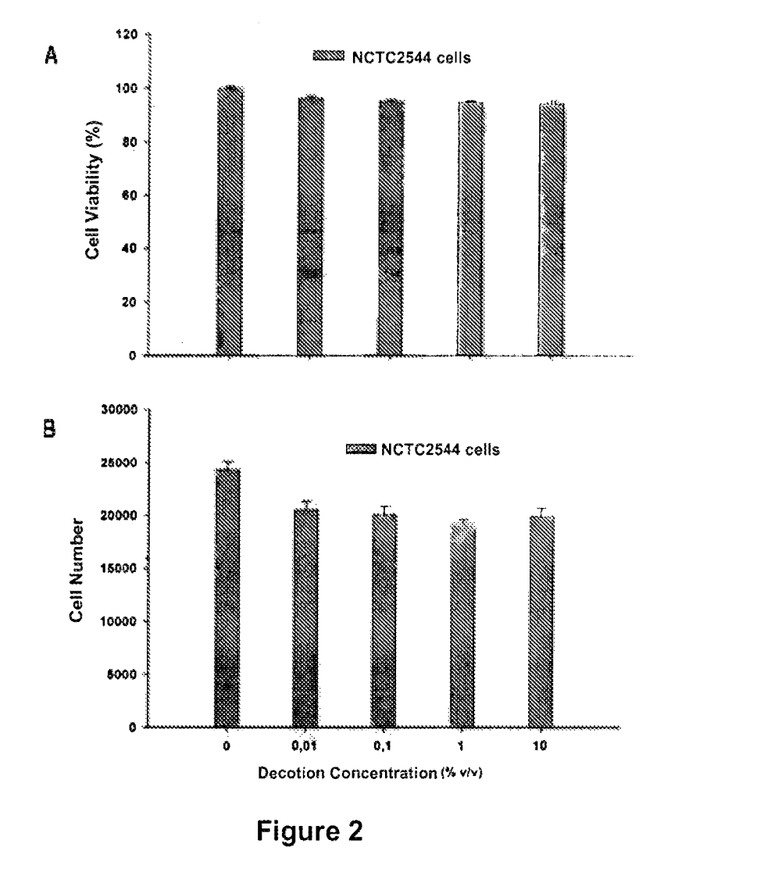
FIG. 2: Toxicologic evaluation at 24 h of a DL extract in human keratinocytes (NCTC2544 cells) by MTT assay: A) Percent cell viability; B) Cell number. Each experiment is the average of three different assessments±standard deviation.
Figure 3:
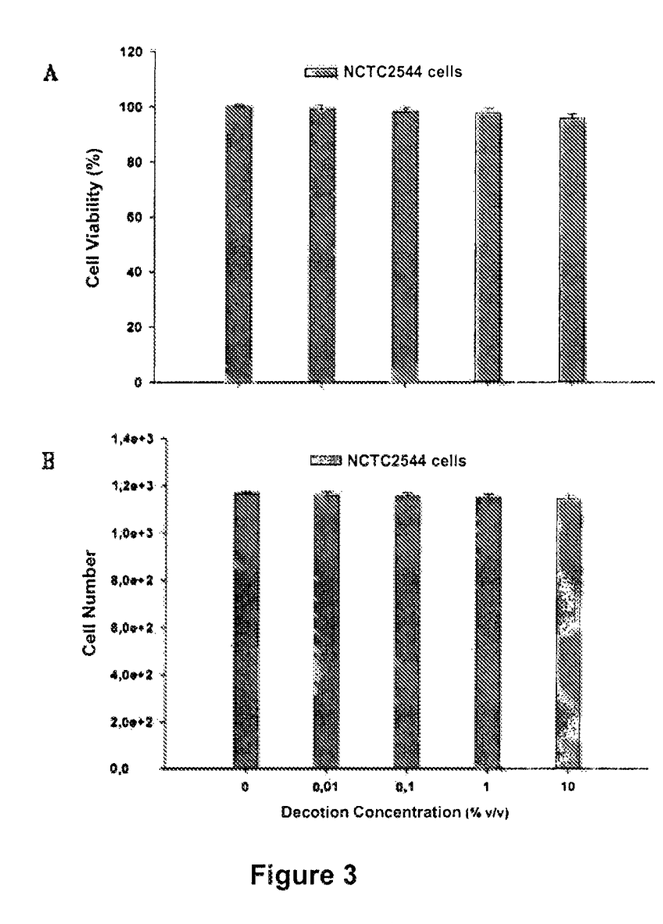
FIG. 3: Toxicologic evaluation at 72 h of a DL extract in human keratinocytes (NCTC2544 cells) by MTT assay: A) Percent cell viability; B) Cell number. Each experiment is the average of three different assessments±standard deviation.

The experimental data illustrated in FIG. 2 show that the structural and functional integrity of NCTC2544, expressed as cell viability, is above 94% at all the decoction extract concentrations used (0.01, 0.1, 1 and 10% v/v) after 24 h of treatment. Non-significant differences in terms of cell viability variations were seen increasing the decoction percentage from 0.01 to 10% v/v (FIG. 2a), possibly because the components of the phytocomplex extracted from the vegetal matrix do not activate mechanisms able to induce adverse reactions in human keratinocytes and are completely biocompatible with our body's defense mechanisms. The experimental results also evidenced that the human keratinocyte number is always higher than 19,000 cells/0.1 ml independently from the v/v concentrations of decoction solution used (FIG. 2b).

In Vivo Evaluation of the Antipsoriatic Activity

The study was carried out using the DL decoction in 30 patients to whom the study protocol was explained and who gave their informed consent (now docketed at the medical practice were the study was carried out). Four patients were treated with a mixture of DL dried and chopped leaves, mixed with glycerin (glyceric mixture).

Treatment with DL Decoction

Figure 5:
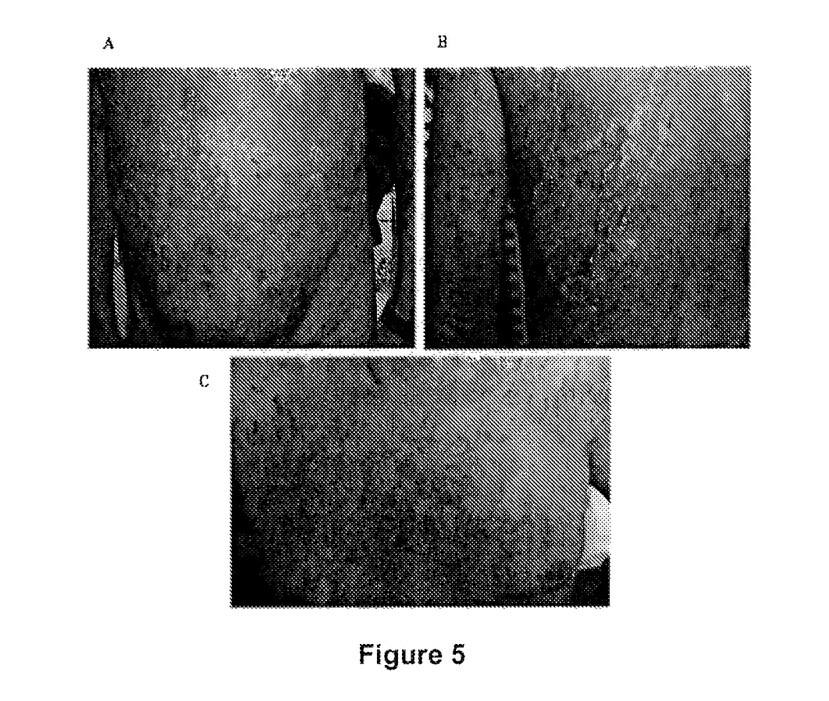
FIG. 5: Body distribution of psoriatic plaques at the start of treatment in a subject suffering from psoriasis (B.R.): A) front, B) back, C) frontal enlargement.

Pictures were taken before the treatment (with the subjects' consent) as a record of the baseline pathology and to evaluate the effectiveness of the proposed treatment (FIG. 5).

The patients were asked to proceed with the treatment twice a day by frictioning the decoction with a cotton gauze.

After plaque remission, the treatment was given once a day for 1 month.

Figure 6:
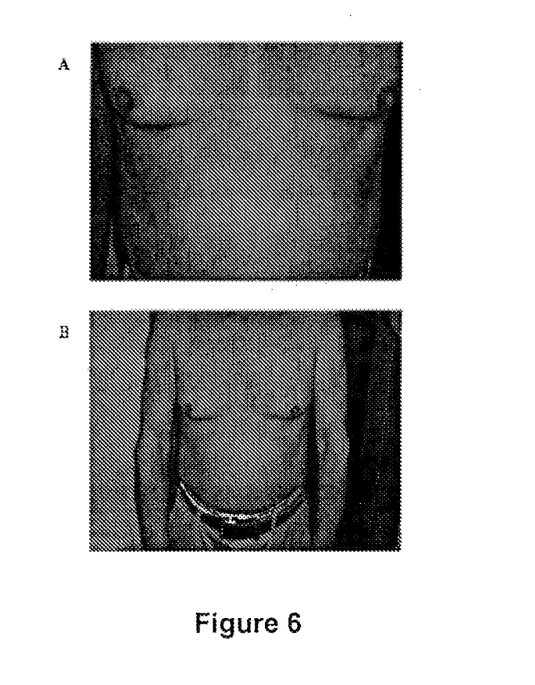
FIG. 6: Regression of the psoriatic plaques in the same subject of FIG. 5 after daily application of a solution of decoction: A) frontal enlargement, B) front.

All the patients treated with the decoction showed a total psoriatic plaques remission already after 20 days of treatment as shown by the enclosed pictures (FIG. 6).

Treatment with Dried DL Leaves

The same study as the previous one was repeated using the glyceric mixture twice a day.

Figure 7:
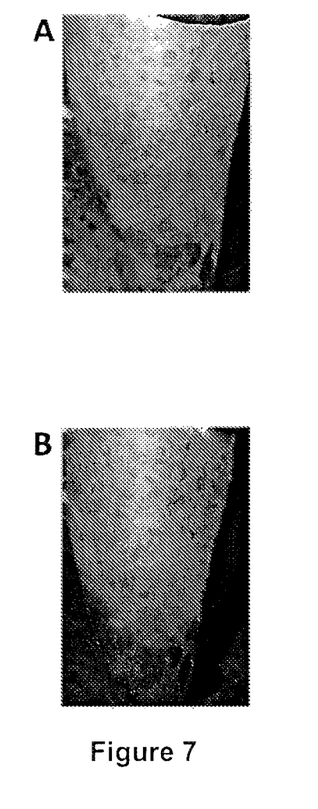
FIG. 7: Psoriatic plaques before (A) and after (B) the daily application of the glyceric mixture.

Differently from the subjects treated with the decoction, the subjects treated with the dried leaves did not show, even after one month of treatment, any significant improvement (FIG. 7).

Preparation of Technological Formulations Containing the DL Decoction

The DL decoction described in the present invention is meant to be used topically, and is the starting point for different products to be applied to the skin (aqueous gels, emulsions, detergent products, lotions).

For example, the following formulations were prepared (all the products used are available on the market and are known in the cosmetic and cosmeceutical preparations field):

| GEL-1 | |
|---|---|
| DL extract in water | 0.5-5% |
| Hydroxypropyl cellulose | 2.5% |
| Preservative | 0.2% |
| Water | q.s. to 100 |

The extract is added to the preserved water, heated to 50° C. and the hydroxypropyl cellulose is then added. The solution is vigorously stirred.

| GEL-2 | |
|---|---|
| DL extract in water | 0.5-5% |
| Carbomer | 1.5% |
| Preservative | 0.2% |
| Triethanolamine | q.s. to pH 4.5 |
| Water | q.s. to 100 |

The extract is added to the preserved water, the solution is stirred adjusting pH with triethanolamine.

| O/W EMULSION | |
|---|---|
| Oily Phase | |
| Caprylic/capric triglyceride | 7.5% |
| PEG 15 Stearyl Ether | 7.5% |
| Isohexadecane | 15% |
| Silicon oil | 5% |
| PEG-10 Glyceryloleate Isohexacontane Succinate | 4% |
| Aqueous Phase | |
| DL extract in water | 0.5-5% |
| Distilled water | q.s. to 100 |
| Carbomer | 2% |
| Preservative | 0.2% |

The O/W emulsion is prepared by adding at 75° C. the oily phase to the aqueous phase under continuous and light stirring. The preparation of the emulsion is carried out in an open turboemulsifier.

REFERENCES

[1] H. Fleisch, A. Reszka, G. A. Rodan, M. Rogers, Bisphosphonates-mechanism of action, in: J. P. Bilezikian, L. G. Raisz, G. A. Rodan (Eds.), Principles of Bone Biology, 2nd ed., Academic Press, San Diego, 2002, pp. 1361-1385.

[2] M. D. Fancis, I. Fogelman, 99mTc diphosphonate uptake mechanism on bone, in: I. Fogelman (Ed.), Bone Scanning in Clinical Pactice, Springer-Verlag, New York, 1987, pp. 7-17.

[3] H. M. Lamb, D. Faulds. Samarium 153Sm lexidronam, Drugs Aging 1997, 11, 413-418.

[4] USA Patent Application 20090123383, Frangioni, Jhon, "Non isotopic detection of osteoblastic activity in vivo using modified bisphosphonates".

[5] J. D. Wang, S. C. Miller, M. Sima, P. Kopeckova, J. Kopecek. Synthesis of polymeric bone-targeting drug delivery systems. Bioconjug. Chem. 2003, 14, 853-859

[6] Frank S. D'Amelio Sr. Botanicals: A Phytocosmetic Desk Reference. CRC Press; 1st edition (Dec. 21, 1998)

[7] Stout, G. H.; Balkenhol, W. G.; Poling, M.; Hickernell, G. L. "*Isolation and structure of daphnetoxin, the poisonous principle of Daphne species*". 1970 J Am Chem Soc, 92(4), 1070-1071

The invention claimed is:

1. A pharmaceutical, cosmetic or cosmeceutical formulation comprising:
   (a) a phytocomplex concentrate extracted from a *Daphne laureola* plant or plant part, wherein the phytocomplex concentrate is present in the pharmaceutical, cosmetic or cosmeceutical formulation in an amount sufficient to have anti-psoriatic activity on human keratinocytes or fibroblasts, and
   (b) a pharmaceutically, cosmetically or cosmeceutically acceptable component or a topical emollient,
   wherein the phytocomplex concentrate is prepared from the *Daphne laureola* plant or plant part by a method comprising:
   (1)
      (i) Preparing an infusion of the *Daphne laureola* plant or plant part by a method comprising steeping the *Daphne laureola* plant or plant part in previously boiled water or a polar solvent, thereby extracting the phytocomplex into the water or polar solvent;
      (ii) preparing a decoction of the *Daphne laureola* plant or plant part by a method comprising steeping the *Daphne laureola* plant or plant part in cold water, then bring the water to a boil, thereby extracting the phytocomplex into the water;
      (iii) steeping the *Daphne laureola* plant or plant part in an alcoholic or hydroalcoholic solution, thereby extracting the phytocomplex into the alcoholic or hydroalcoholic solution;
      (iv) contacting the *Daphne laureola* plant or plant part with a supercritical fluid, thereby extracting the phytocomplex into the supercritical fluid;
      (v) percolating the *Daphne laureola* plant or plant part in a polar solvent under continuous agitation, optionally assisted by ultrasound and/or microwave, thereby extracting the phytocomplex into the polar solvent; or
      (vi) any combination of (i) to (v); and
   (2) preparing the phytocomplex concentrate from the water, polar solvent, alcoholic or hydroalcoholic solution, or supercritical fluid by removing all or a portion of the water, polar solvent, alcoholic or hydroalcoholic solution, or supercritical fluid,
   wherein optionally the concentrate of the phytocomplex is prepared by a method comprising evaporation of the water, polar solvent, alcoholic or hydroalcoholic solution, or supercritical fluid, or lyophilization of the phytocomplex-comprising water, polar solvent, alcoholic or hydroalcoholic solution, or supercritical fluid, and optionally the concentrate comprises a liquid, a semisolid or a dry extract,
   wherein the pharmaceutical, cosmetic or cosmeceutical is formulated for topical application.

2. The pharmaceutical, cosmetic or cosmeceutical formulation of claim 1, formulated as a liquid, an emulsion, a lotion, a detergent, an aqueous gel, a semifluid or a dry form.

3. The pharmaceutical, cosmetic or cosmeceutical formulation of claim 1, wherein the pharmaceutical, cosmetic or cosmeceutical formulation further comprises vaseline, a cortisone formulation, a reducing agent, a keratolytic agent, a vitamin D analog; a retinoid, a cyclosporin A, a monoclonal antibody, a cytokine, a fusion proteins or a tissue growth factor.

4. The pharmaceutical, cosmetic or cosmeceutical formulation of claim 3, wherein the additional pharmaceutically, cosmetically and cosmeceutically acceptable component is selected from the group consisting of: emollients, moisturizers, thickeners, emulsifiers, colorings, detergents, disinfectants, antioxidants, buffers, matting agents, exfoliating agents, aromas and similar, essential oils, vitamins, UV filters, collagen, elastin and mixtures thereof.

5. The pharmaceutical, cosmetic or cosmeceutical formulation of claim 1, formulated for topical application as liquid formulations, gels, lotions, milks, emulsions, foams; or formulated as solid or semisolid formulations, or formulated as a cream, an ointment, or a stick.

6. The pharmaceutical, cosmetic or cosmeceutical formulation of claim 1, formulated for topical application as: shampoo, cleansing milk, aqueous tonic, aqueous solution, alcoholic solution, hydroalcoholic solution, mask, water-based gel, lipogel, face and body oil, or medicated patches.

7. The pharmaceutical, cosmetic or cosmeceutical formulation of claim 1, formulated as topical application in the treatment of psoriasis.

8. The pharmaceutical, cosmetic or cosmeceutical formulation of claim 7, wherein the psoriasis is selected from the group consisting of: plaque psoriasis, guttate psoriasis, pustular psoriasis, erythrodermal psoriasis, seborrhoic psoriasis, and amiantaceous psoriasis.

9. The pharmaceutical, cosmetic or cosmeceutical formulation of claim 1, wherein the *Daphne laureola* phytocomplex concentrate prepared from fresh or dried flowers, fruits, leaves, stalks or roots of a *Daphne laureola* plant.

10. The pharmaceutical, cosmetic or cosmeceutical formulation of claim 1, formulated as a cleansing milk comprising from between about 0.1 to 5% of dry extract.

11. The pharmaceutical, cosmetic or cosmeceutical formulation of claim 1, formulated as an emulsion comprising from between about 0.5 to 10% of dry extract.

12. The pharmaceutical, cosmetic or cosmeceutical formulation of claim 1, formulated as a water-based gel comprising from between about 5 to 20% of dry extract.

13. The pharmaceutical, cosmetic or cosmeceutical formulation of claim 1, formulated as an aqueous lotion comprising from between about 0.5 to 20% of dry extract.

14. The pharmaceutical, cosmetic or cosmeceutical formulation of claim 1, formulated as a medicated patch comprising from between about 5 to 2% of dry extract.

15. The pharmaceutical, cosmetic or cosmeceutical formulation of claim 1, formulated as a shampoo comprising from between about 0.5 to 10% of dry extract.

16. The pharmaceutical, cosmetic or cosmeceutical formulation of claim 4, wherein the additional pharmaceutically, cosmetically and cosmeceutically acceptable component comprises caprylic/capric triglyceride; PEG 15 Stearyl Ether; Isohexadecane; Silicon oil; PEG-10 Glyceryloleate Isohexacontane Succinate, or a combination thereof.

* * * * *